(12) United States Patent
Matsukawa et al.

(10) Patent No.: US 11,414,697 B2
(45) Date of Patent: Aug. 16, 2022

(54) REACTION CONTAINER AND BIOCHEMICAL ANALYSIS METHOD

(71) Applicant: TOPPAN PRINTING CO., LTD., Taito-ku (JP)

(72) Inventors: Masahiro Matsukawa, Taito-ku (JP); Yoichi Makino, Taito-ku (JP); Akihiro Hoshino, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 617 days.

(21) Appl. No.: 16/171,630

(22) Filed: Oct. 26, 2018

(65) Prior Publication Data

US 2019/0062821 A1 Feb. 28, 2019

Related U.S. Application Data

(63) Continuation of application No. PCT/JP2017/016828, filed on Apr. 27, 2017.

(30) Foreign Application Priority Data

Apr. 27, 2016 (JP) .............................. JP2016-089362

(51) Int. Cl.
*B01L 3/00* (2006.01)
*C12M 1/34* (2006.01)
(Continued)

(52) U.S. Cl.
CPC ............ *C12Q 1/6844* (2013.01); *B01L 3/502* (2013.01); *B01L 3/50853* (2013.01); *C12M 1/00* (2013.01);
(Continued)

(58) Field of Classification Search
CPC ........ C12Q 1/6844; C12Q 1/68; G01N 21/00; G01N 37/00; G01N 21/64; G01N 33/50;
(Continued)

(56) References Cited

U.S. PATENT DOCUMENTS 9,375,696 B2 9/2016 Shimizu
2007/0059763 A1* 3/2007 Okano ................. G01N 33/566
435/7.1

(Continued)

FOREIGN PATENT DOCUMENTS

EP 2 589 952 A1 5/2013
JP 2007-187582 A 7/2007
(Continued)

OTHER PUBLICATIONS

Kataoka, Masatoshi et al "English machine translation WO2014007190 A".*

(Continued)

*Primary Examiner* — Liban M Hassan
(74) *Attorney, Agent, or Firm* — Oblon, McClelland, Maier & Neustadt, L.L.P.

(57) ABSTRACT

A reaction container including a transparent base having a first surface having at least one region where recessed portions are formed and recessed from the first surface, and a cover member positioned such that the cover member forms a gap from the first surface inside the region and is welded to the transparent base outside the region. The cover member absorbs infrared light and transmits light having a wavelength within a range of visible light.

20 Claims, 6 Drawing Sheets

(51) Int. Cl.
*C12Q 1/6844* (2018.01)
*G01N 21/64* (2006.01)
*G01N 33/68* (2006.01)
*C12Q 1/68* (2018.01)
*G01N 21/00* (2006.01)
*C12M 1/00* (2006.01)
*G01N 37/00* (2006.01)
*C12N 15/09* (2006.01)
*G01N 33/50* (2006.01)
*C12N 15/10* (2006.01)

(52) U.S. Cl.
CPC ........... *C12M 1/3446* (2013.01); *C12N 15/09* (2013.01); *C12Q 1/68* (2013.01); *G01N 21/00* (2013.01); *G01N 21/64* (2013.01); *G01N 21/6428* (2013.01); *G01N 33/50* (2013.01); *G01N 33/68* (2013.01); *G01N 37/00* (2013.01); *B01L 2200/0689* (2013.01); *C12N 15/1013* (2013.01)

(58) Field of Classification Search
CPC ............... G01N 21/6428; G01N 33/68; G01N 21/6452; G01N 2021/0325; G01N 2021/0389; G01N 21/0303; G01N 21/645; G01N 2021/6482; G01N 2201/0686; C12M 1/00; C12M 1/3446; C12N 15/09; C12N 15/1013; B01L 3/50853; B01L 3/502; B01L 2200/0689; B01L 2300/0819; B01L 2300/0645; B01L 2300/0654; B01L 2300/04; B01L 2300/12; B01L 2300/168; B01L 3/50851

USPC ...................................................... 435/289.1
See application file for complete search history.

(56) References Cited

U.S. PATENT DOCUMENTS

| | | | |
|---|---|---|---|
| 2008/0277606 | A1 | 11/2008 | Wang et al. |
| 2012/0015828 | A1 | 1/2012 | Ozawa et al. |
| 2013/0089929 | A1* | 4/2013 | Joo .................. C12M 23/16 435/450 |
| 2013/0099143 | A1 | 4/2013 | Mogami et al. |
| 2015/0337355 | A1 | 11/2015 | Araki et al. |
| 2016/0333400 | A1 | 11/2016 | Makino et al. |

FOREIGN PATENT DOCUMENTS

| | | | | |
|---|---|---|---|---|
| JP | 2008-216121 A | 9/2008 | | |
| JP | 2012-132935 A | 7/2012 | | |
| WO | WO 2013/151135 A1 | 10/2013 | | |
| WO | WO 2014/007190 A1 | 1/2014 | | |
| WO | WO-2014007190 A1 * | 1/2014 | ......... | G01N 15/1459 |
| WO | WO 2015/115635 A1 | 8/2015 | | |

OTHER PUBLICATIONS

European Office Action dated Sep. 11, 2020 in European Patent Application No. 17789682.6, 7 pages.
International Search Report dated Jul. 25, 2017 in PCT/JP2017/016828, filed Apr. 27, 2017, 5 pages.
Extended European Search Report dated Oct. 17, 2019, in Patent Application No. 17789682.6, 8 pages.

* cited by examiner

REACTION CONTAINER AND BIOCHEMICAL ANALYSIS METHOD

CROSS-REFERENCE TO RELATED APPLICATIONS

The present application is a continuation of International Application No. PCT/JP2017/016828, filed Apr. 27, 2017, which is based upon and claims the benefits of priority to Japanese Application No. 2016-089362, filed Apr. 27, 2016. The entire contents of these applications are incorporated herein by reference.

BACKGROUND OF THE INVENTION

Field of the Invention

The present invention relates to a reaction container and a biochemical analysis method.

Discussion of the Background

Conventionally, performing diagnosis of disease and predisposition by analyzing biomolecules is known.

For example, diagnosis of predisposition by analysis of single nucleotide polymorphism (SNP) recorded in DNA, judgment for administering anticancer agents by somatic mutation analysis, measures against infectious diseases by viral protein analysis, and the like are known.

For example, in cancer remedies, it has been suggested that quantifying the amplified amount (copy number) of EGFR (epidermal growth factor receptor) gene mutation before and after the administration of an EGFR-TKI (tyrosine kinase inhibitor) can be used as an indicator of the therapeutic effect. Conventionally, quantification using real-time PCR (polymerase chain reaction) has been performed. However, it has been found that changes in the total amount of nucleic acid used in the examination affects the quantitativeness, and recently digital PCR technology is being developed in which the total amount of nucleic acid does not affect the quantitativeness.

Digital PCR technology is a kind of digital analysis technology for quantifying nucleic acids in samples by dividing a mixture of PCR reagent and nucleic acids into a large number of microdroplets and performing PCR amplification on these microdroplets using the nucleic acid to be detected from among the nucleic acids in the mixture as a template, then detecting signals such as fluorescence or the like by PCR amplification from the microdroplets that include the template nucleic acid, and finding the ratio of microdroplets from which signals were detected with respect to the total number of microdroplets.

Digital analysis technology requires an enclosed container for sealing in fluorescent beads that emit light by combining with the mixture and microdroplets, and for making it possible to read the fluorescent beads with a microscope. In this enclosed container, in order to be able to individually distinguish between each fluorescent bead and droplet, micro holes for accommodating beads are uniformly arranged on the bottom surface of the container; the beads are then poured in so as to be accommodated in the respective holes, and enclosed in the container.

In digital PCR, the mixture of PCR reaction reagent and the nucleic acids is diluted so that the number of template nucleic acids present in a single microdroplet is zero to one. In digital PCR, in order to increase the sensitivity of nucleic acid amplification, and to perform nucleic amplification simultaneously on a large number of microdroplets, preferably the volume of each microdroplet is small. For example, Patent Literature 1 discloses a microarray reaction container formed so that the volume of each well is 6 nl (nanoliters). In addition, Patent Literature 2 discloses a method in which a sample is introduced into each well by allowing a sample to flow through a flow path over a microarray in which a large number of wells having a depth of 3 μm and diameter of 5 μm are formed in the flow path, after which the excess reagent in the flow path is expelled with a sealant liquid.

PTL 1 WO2013/151135
PTL 2 WO2014/007190

SUMMARY OF THE INVENTION

According to an aspect of the present invention, a reaction container includes a transparent base having a first surface having at least one region where recessed portions are formed and recessed from the first surface, and a cover member positioned such that the cover member forms a gap from the first surface inside the region and is welded to the transparent base outside the region. The cover member absorbs infrared light and transmits light having a wavelength within a range of visible light.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
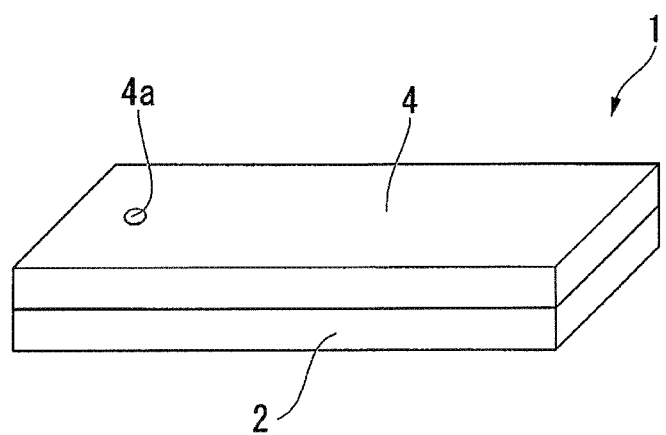
FIG. 1 is a schematic view of a reaction container according to an embodiment of the present invention.

The embodiments will now be described with reference to the accompanying drawings, wherein like reference numerals designate corresponding or identical elements throughout the various drawings.

An embodiment of the present invention will now be described.

Figure 2:
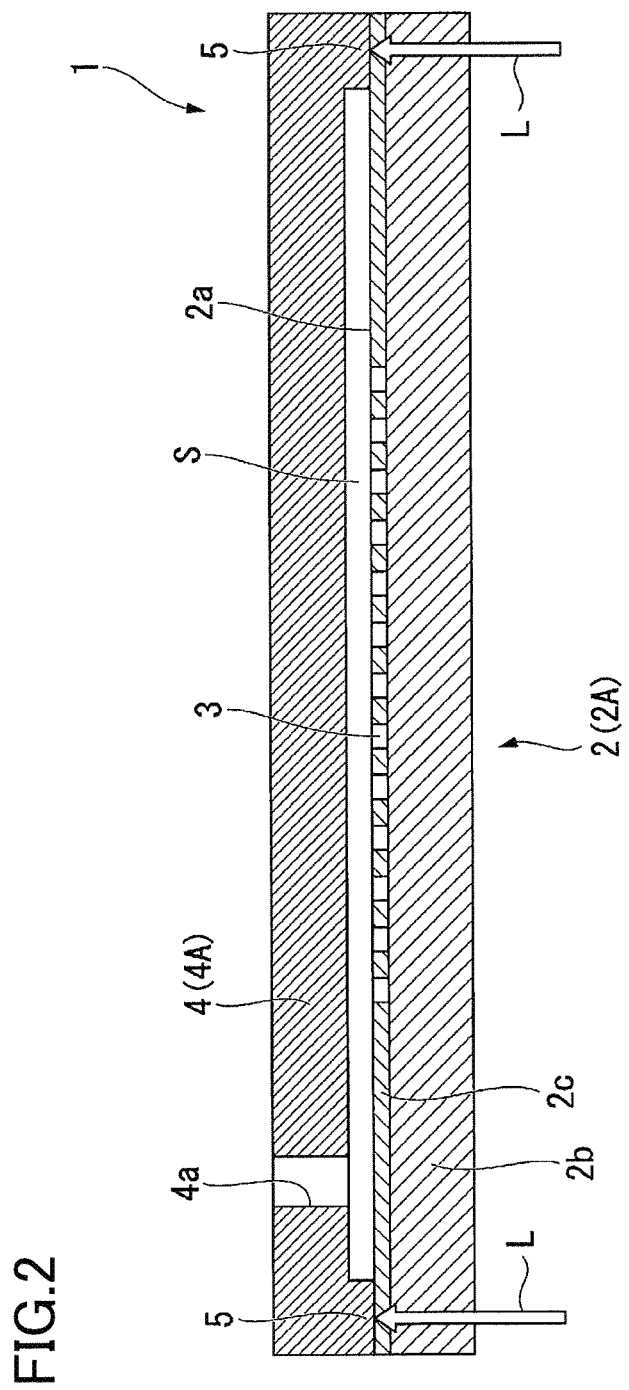
FIG. 2 is a cross-sectional view of a reaction container according to an embodiment of the present invention.

FIG. 1 is a schematic view of a reaction container 1 of this embodiment. FIG. 2 is a cross-sectional view of the reaction container 1 of this embodiment.

As illustrated in FIG. 1 and FIG. 2, the reaction container of this embodiment includes a base 2 and a cover member 4.

The base 2 is formed using a light transmitting resin. The base 2 of this embodiment is substantially transparent.

The base 2 has a plurality of recessed portions 3. The recessed portions 3 of the base 2 are open on the surface (first surface 2a) of the base 2. The shape, dimensions and arrangement of the recessed portions 3 are not particularly limited. In this embodiment, a plurality of recessed portions 3 having the same size and capable of accommodating a predetermined amount of sample used in the biochemical analysis performed using the reaction container 1 is formed in the base 2. Moreover, in the case where microbeads are used in the biochemical analysis performed using the reaction container 1, recessed portions 3 having the same size formed in the base 2 have a shape and dimension capable of accommodating one microbead, and are capable of accommodating a fixed amount of sample that includes microbeads.

In this embodiment, for example, recessed portions 3 having a volume of approximately 15 μl capable of accommodating microbeads having a diameter of no less than 2 μm and no more than 5 μm are formed in the base 2 and arranged so as to form a triangular lattice shape or square lattice shape when viewed from a direction perpendicular to the first surface 2a. For example, in the case of presuming the accommodation of microbeads having a diameter of 3 μm, the diameter of the recessed portions 3 is, for example, 5 μm, and the depth of the recessed portions 3 is, for example, 3 μm.

A region of the first surface 2a of the base 2 that includes a plurality of recessed portions 3 is a region filled with one kind of sample as a target of analysis by the biochemical analysis. Inside this region, a gap (flow path) S is opened up between the base 2 and the cover member 4.

The cover member 4 is welded to the base 2. A spacer portion 5 for regulating the size of the gap S inside the above-mentioned region of the base 2 is arranged in the cover member 4 so as to surround this region. The spacer portion 5 is part of the cover member 4 and is formed using resin. The spacer portion 5 is provided so as to protrude toward the base 2 from the outer peripheral edge portion of the bottom surface of the cover member 4. The spacer portion 5 is welded to the base 2 by a laser transmission welding method. In addition, an opening 4a is formed in the cover member 4 for injecting a sample and the like into the gap between the cover member 4 and the base 2. That is, the base 2 and the cover member 4 are welded together via the spacer portion 5, and the region surrounded by the base 2, the cover member 4 and the spacer portion 5 becomes the flow path (gap) S.

The cover member 4 has infrared absorbance. For example, the cover member 4 is formed using a thermoplastic resin that includes an additive for increasing the absorption of infrared rays. Furthermore, the cover member 4 is capable of transmitting light in at least part of the visible light wavelength range. For example, the total light transmittance of the cover member 4 is lower than the total light transmittance of the base 2, but is high enough to ensure the brightness required for bright-field observation. In addition, the light transmittance in the infrared range of the cover member 4 may be lower than the light transmittance in the visible light range. For example, together with having light transmittance in the infrared range, the cover member 4 may have enough light transmittance to be substantially transparent to visible light. It is preferable that the surface of the cover member 4 that is in contact with the base 2 have low infrared reflectance.

The cover member 4 has substantially uniform light transmittance throughout the entire member. For example, the cover member 4 is formed using a thermoplastic resin that includes a cycloolefin polymer (COP) and/or an acrylic resin. The light transmittance of the cover member 4 may have a gradient in the thickness direction of the cover member 4. For example, the light transmittance on the base 2 side of the cover member 4 may be low and the light transmittance on the opposite side from the base 2 may be high. In this case, the cover member 4 has the highest infrared absorbance on the first surface 2a side of the base 2.

In this embodiment, preferably the total light transmittance of the cover member 4 is 0.01 to 60%, more preferably 0.1 to 60%, and even more preferably 25 to 50%. In the case where the total light transmittance of the cover member 4 is 0.01% or more, it is possible to easily visually recognize light that is reflected from the opposite side of the cover member 4. In the case where the total light transmittance of the cover member 4 is 0.1% or more, the exposure time during observation with a microscope can be reduced. Moreover, in the case where the total light transmittance of the cover member 4 is 60% or less, good laser welding can be performed without the failure of the mold. Furthermore, in the case where the total light transmittance of the cover member 4 is 25% or more, sufficient brightness in bright-field observation can be obtained. In addition, in the case where the total light transmittance of the cover member 4 is 50% or less, autofluorescence of the cover member 4 during observation by a microscope can be reduced.

The operation of the reaction container 1 of this embodiment will be explained together with the manufacturing step of the reaction container 1.

For the manufacturing of the reaction container of this embodiment, a first plate-shaped member 2A made of a resin that will be the material of the base 2, and a second plate-shaped member 4A made of a resin that will be the material of the cover member 4 are prepared (refer to FIG. 2).

Then, the first plate-shaped member 2A and the second plate-shaped member 4A are processed.

A plurality of recessed portions 3 is formed in one surface in the plate thickness direction of the first plate-shaped member 2A. As an example, as illustrated in FIG. 1, a CYTOP (registered trademark of Asahi Glass) layer 2c in which minute holes having a diameter of 5 μm, for example, are arranged and open in a lattice shape inside a 10 mm square region is formed on one surface in the plate thickness direction of a resin plate 2b that will be the material of the first plate-shaped member 2A. In other words, the first plate-shaped member 2A has a resin plate 2b and a CYTOP layer 2c. The minute holes formed in the CYTOP (registered trademark) are the recessed portions 3. The first plate-shaped member 2A is obtained, for example, by forming CYTOP (registered trademark) on a substantially transparent thermoplastic resin, and has enough light transmittance to be regarded as being substantially transparent in at least the visible light and infrared light range. In addition, the first plate-shaped member may be integrally molded using resin.

Examples of the material of a first plate-shaped member made using resin include a cycloolefin polymer, a cycloolefin copolymer, silicone, polypropylene, polycarbonate, polystyrene, polyethylene, polyvinyl acetate, a fluororesin, an amorphous fluororesin, and the like. These materials given as examples of the first plate-shaped member are merely examples, and the material of the first plate-shaped member is not limited to these materials.

The second plate-shaped member 4A is formed so as to have the spacer portion 5 on the surface facing the first plate-shaped member 2A at the time of assembly. For example, the second plate-shaped member 4A is molded into a plate shape having the spacer portion 5 by using a molding die to mold a thermoplastic resin fluid in which additives are mixed so that the total light transmittance is 25% or more and 50% or less. In addition, an opening 4a is formed in the second plate-shaped member 4A for injecting sample or the like. The surface of the molded second plate-shaped member 4A facing the first plate-shaped member 2A side undergoes surface treatment to increase water repellency. For example, a coating agent layer is formed by applying a water repellent coating agent to the surface of the molded second plate-shaped member 4A facing the first plate-shaped member 2A.

After the first plate-shaped member 2A and the second plate-shaped member 4A are formed as described above, the first plate-shaped member 2A and the second plate-shaped member 4A are placed together overlapping each other so that the spacer portion 5 of the second plate-shaped member 4A comes in contact with the surface of the first plate-shaped member 2A on the side where the recessed portions 3 are formed (this surface becomes the first surface 2a of the base 2). Furthermore, in a state in which the first plate-shaped member 2A and the second plate-shaped member 4A overlap each other as described above, a laser L (refer to FIG. 2) having a long wavelength that is equal to or greater than that of near infrared rays (for example, a wavelength of 800 nm or more) is passed through the first plate-shaped member 2A and irradiated on the spacer portion 5 of the second plate-shaped member 4A. As the laser irradiated on the spacer portion 5, a solid-state laser (for example, YAG laser), or a semiconductor laser (laser diode) can be used. The usable wavelength of the laser can be within the range 800 nm or more and 1000 nm or less.

The laser irradiated on the spacer portion 5 is hardly absorbed by the first plate-shaped member 2A and is absorbed by the spacer portion 5, so the spacer portion 5 is heated. As a result, the site of the spacer portion 5 where the laser is irradiated melts, and further, the portion of the first plate-shaped member 2A that is in contact with the spacer portion 5 melts due to the heat transmitted from the spacer portion 5. After irradiation of the laser on the spacer portion 5 ends, the temperature of the melted portions of the spacer portion 5 and the first plate-shaped member 2A lowers and the melted portions are integrally hardened. As a result, the first plate-shaped member 2A and the second plate-shaped member 4A are welded at the spacer portion 5. The first plate-shaped member 2A becomes the base 2 of the reaction container 1, and the second plate-shaped member 4A becomes the cover member 4 of the reaction container 1.

In the reaction container 1 of this embodiment, the base 2 and the cover member 4 are welded together by a laser transmission welding method, so precise and reliable welding is possible, and it becomes difficult for sample or the like that is injected between the base 2 and the cover member 4 to leak. As a result, with the reaction container 1 of this embodiment, reproducibility of biochemical analysis using the reaction container 1 is excellent.

Particularly, in this embodiment, the base 2 is substantially transparent, and the total light transmittance of the cover member 4 is 25% or more, so sufficient brightness for bright-field observation can be obtained.

In this way, with the reaction container 1 of this embodiment, resin having light transmittance is welded with high accuracy, and sufficient brightness for bright-field observation can be obtained. The total light transmittance (optical density) of the cover member 4 can be measured using a known measurement method. It is also possible to estimate, from the visible light transmittance, the transmittance of light having a long wavelength that is equal to or greater than that of infrared rays. For example, in the case where the cover member is formed using COP, when the transmittance of visible light is 92%, the transmittance of light having a long wavelength that is equal to or greater than that of infrared rays becomes 90%.

An example of biochemical analysis using the reaction container 1 of this embodiment will be described.

The reaction container 1 of this embodiment can be used for measuring the density of a target object to be analyzed in a sample by observing a signal by performing a signal amplification reaction on the sample.

First, a sample that is diluted so that one molecule of the target substance to be detected will enter into the recessed portions 3 of the reaction container 1 is fed from the opening 4a in the cover member 4 into the gap between the base 2 and the cover member 4 (liquid feeding step). The sample that is fed in the liquid feeding step includes DNA, RNA miRNA, mRNA or protein as the target object to be analyzed. The sample also includes a detection reagent for the target object to be analyzed. The detection reagent includes enzymes, buffer substances or the like. In the case where the target object to be analyzed is a nucleic acid, for example, the enzyme included in the reagent is selected to correspond to the content of the biochemical reaction in order to perform a biochemical reaction, such as an enzymatic reaction or the like on the template nucleic acid related to the target object to be analyzed. The biochemical reaction to the template nucleic acid is, for example, a reaction such that signal amplification occurs under conditions in which the template nucleic acid is present. The reagent is, for example, selected according to a method capable of detecting a nucleic acid. More specifically, the reagents of this embodiment include reagents that are used in an Invader (registered trademark)

method, a LAMP (registered trademark) method, a TaqMan (registered trademark) method, a fluorescent probe method, or other method.

In the liquid feeding step, the sample that is fed to the gap between the base 2 and the cover member 4 is accommodated inside the plurality of recessed portions 3.

Then, an oil-based sealant liquid is fed from the opening 4a in the cover member 4 to the gap between the base 2 and the cover member 4 to individually seal the plurality of recessed portions 3 (sealing step). The sealant liquid is one of either a fluorine-based oil or a silicone-based oil, or a mixture or the like of these.

In the sealing step, the sealant liquid replaces sample that is not accommodated in the recessed portions 3 of the sample fed to the gap between the base 2 and the cover member 4 in the liquid feeding step described above. As a result, sealant liquid individually seals the plurality of recessed portions 3, and the recessed portions 3 become independent reaction spaces.

Next, a specified biochemical reaction is performed in the recessed portions 3 (reaction step). In the reaction step of this embodiment, a signal amplification reaction is performed in the recessed portions 3. In other words, a signal is amplified by the reaction step to a level at which the signal is observable so that a signal derived from a specific labeling substance can be detected in the recessed portions 3. Examples of signals include fluorescence, coloring, electric potential change, pH change, and the like. In this embodiment, for example, in the case where a target object to be analyzed and a specific labeling substance are both accommodated in the recessed portions 3, the fluorescent signal is amplified as the signal amplification reaction in the reaction step. The signal amplification reaction is, for example, an enzymatic reaction. As an example, the signal amplification reaction is an isothermal reaction in which a sample that includes an enzyme for signal amplification is accommodated in the recessed portions 3, and in this state, the reaction container 1 is maintained at a constant temperature for a specified amount of time so that a desired enzyme activity is obtained. As a specific example, an Invader reaction can be used as the signal amplification reaction. In this case, an Invader reaction reagent and a template nucleic acid are included in the sample in the recessed portions 3. In the case where the biochemical reaction in the reaction step is an Invader reaction, and both the target object to be analyzed and the specific labeling substance are accommodated in the recessed portions 3 by an enzymatic reaction due to the isothermal reaction, a fluorescent substance is released from the quenching substance, which results in a specified fluorescence signal being emitted corresponding to the excitation light.

After the reaction step, the signal amplified by the signal amplification reaction in the reaction step is observed.

First, in order to identify recessed portions 3 that accommodate the specific labeling substance, the recessed portions 3 are observed for the presence or the absence of microbeads (first observation step).

In the first observation step, bright-field observation is performed using white light that is irradiated in a direction perpendicular to the first surface 2a of the reaction container 1. In the case where microbeads are present in the recessed portions 3, the shadows of the microbeads will be observed, so as a result, of the recessed portions 3 formed in the base 2, the recessed portions 3 that accommodate microbeads can be identified.

In the first observation step, all or part of an image of the region that includes the plurality of recessed portions 3 is captured and stored as an image, and image processing is performed by a computer system.

Next, in the case where the specific labeling substance and the target object to be analyzed are both present in the recessed portions 3, whether or not there is a signal to be amplified by the above-mentioned reaction step is observed (second observation step).

In the second observation step, in the case where the above-mentioned Invader reaction is performed, excitation light that corresponds to the fluorescent substance is irradiated from the base 2 side toward the cover member 4 side through the base 2 into the recessed portions 3, and fluorescence emitted by the fluorescent substance included in the sample is observed from the base 2 side. The base 2 is substantially transparent, so fluorescence observation can be performed with sensitivity equivalent to that of a known reaction container 1 that is used for fluorescence observation.

In the second observation step, all or part of an image of the region that includes the plurality of recessed portions 3 is captured, and stored as an image, and image processing by a computer system is performed.

In this way, with the biochemical analysis method using the reaction container 1 of this embodiment, bright-field observation and fluorescence observation can be performed.

EXPERIMENT EXAMPLES

Experiment examples that clarify the effect that the degree of light transmittance of the cover member 4 has on bright-field observation and fluorescence observation will be described below. In the experiment examples described below, corresponding reference numbers are assigned to the constituent elements corresponding to the reaction container 1 of this embodiment.

In the experiment examples, in order to manufacture the reaction container 10 for the experiments, two plate-shaped members made of a transparent resin were used. Of the two plate-shaped members, the base 2 was formed from one plate-shaped member. A spacer portion 5 was formed using double-sided tape on the other plate-shaped member, and the other plate-shaped member was then adhered to the base 2 in the place of the cover member 4.

A liquid in which fluorescently labeled microbeads were dispersed was injected between the two plate-shaped members, and then the plurality of recessed portions 3 were further sealed individually with a sealant liquid. The state of the fluorescently labeled microbeads accommodated in the recessed portions 3 was observed (bright-field observation and fluorescence observation) using a fluorescence microscope (BX-51, manufactured by Olympus Corporation).

The reaction container 10 for experimentation that was manufactured for the experiment examples was substantially transparent as a whole. In the experiment examples, one of a colored film having light transmittance and a black film having no light transmittance was applied to the reaction container 10 for experimentation and observation was performed. In the experiment examples, each of the above-mentioned films was applied to the plate-shaped member that corresponds to the cover member 4.

Figure 3:
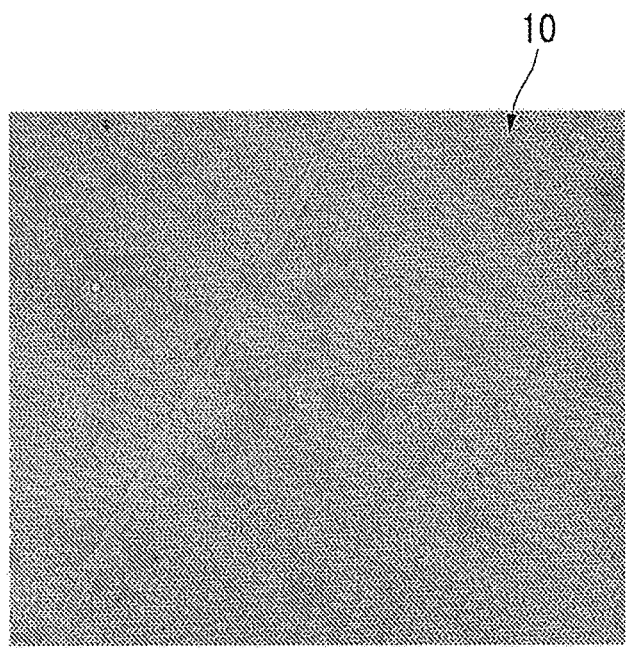
FIG. 3 is an image of an experiment example related to light transmittance of a cover member of a reaction container according to an embodiment of the present invention, and illustrates the results of bright-field observation using a reaction container having a configuration corresponding to a case where the cover member has light transmittance.
Figure 4:
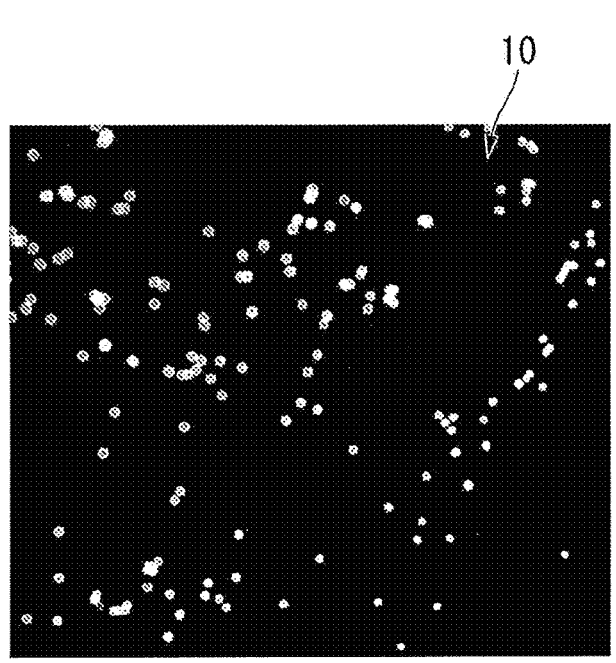
FIG. 4 is an image of an experiment example related to light transmittance of a cover member of a reaction container according to an embodiment of the present invention, and illustrates the results of fluorescence observation using a reaction container having a configuration corresponding to a case where the cover member has light transmittance.

FIG. 3 is an image of an experiment example related to light transmittance of the cover member of the reaction container according to an embodiment of the present invention, and illustrates the result of bright-field observation using a reaction container having configuration corresponding to the case where the cover member is transparent. FIG. 4 is an image of an experiment example related to light transmittance of the cover member of the reaction container according to an embodiment of the present invention, and illustrates the result of fluorescence observation using a reaction container having configuration corresponding to the case where the cover member is transparent.

As illustrated in FIG. 3 and FIG. 4, in the case where neither film is applied to the reaction container 10 for experimentation, an image could be obtained by bright-field observation, and an image could also be obtained by fluorescence observation.

Figure 5:
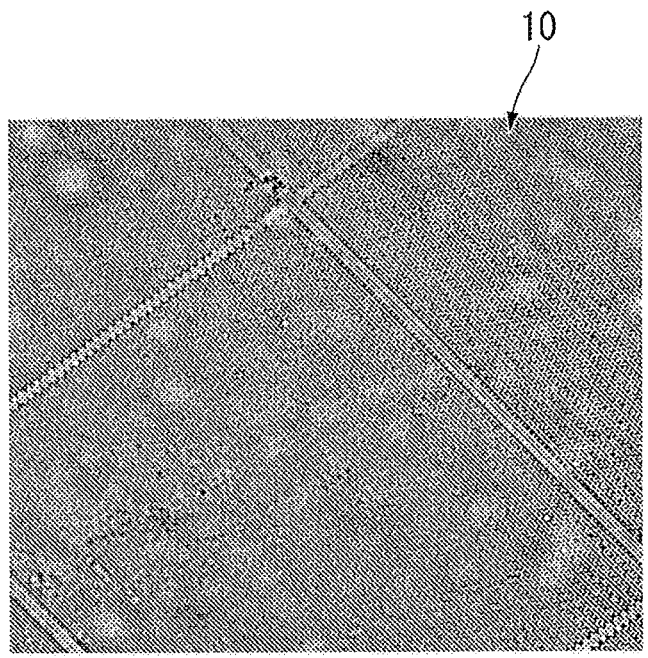
FIG. 5 is an image of an experiment example related to light transmittance of a cover member of a reaction container according to an embodiment of the present invention, and illustrates the results of bright-field observation using a reaction container having a configuration corresponding to a case where the cover member has light transmittance and is colored.
Figure 6:
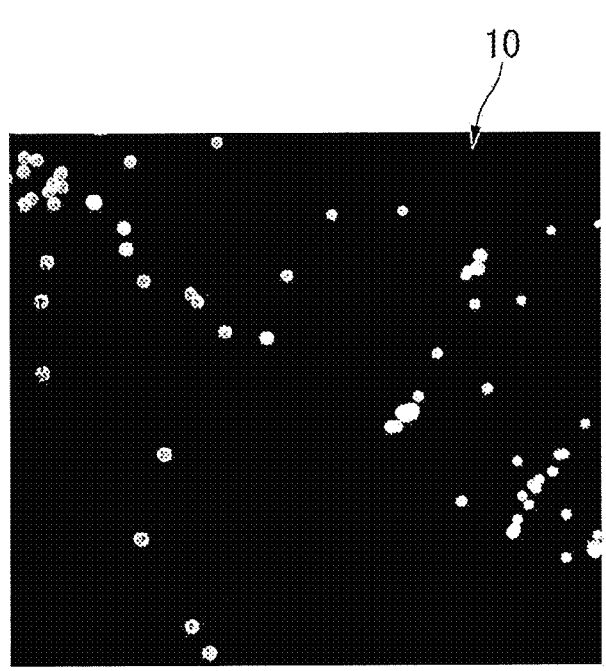
FIG. 6 is an image of an experiment example related to light transmittance of a cover member of a reaction container according to an embodiment of the present invention, and illustrates the results of fluorescence observation using a reaction container having a configuration corresponding to a case where the cover member has light transmittance and is colored.

FIG. 5 is an image of an experiment example related to light transmittance of the cover member of the reaction container according to an embodiment of the present invention, and illustrates the result of bright-field observation using a reaction container having a configuration corresponding to the case where the cover member is colored and has light transmittance. FIG. 6 is an image of an experiment example related to light transmittance of the cover member of the reaction container according to an embodiment of the present invention, and illustrates the result of fluorescence observation using a reaction container having a configuration corresponding to the case where the cover member is colored and has light transmittance.

As illustrated in FIG. 5 and FIG. 6, in the case where the colored film also is applied to the reaction container 10 for experimentation, an image could be obtained by bright-field observation, and an image could also be obtained by fluorescence observation.

Figure 7:
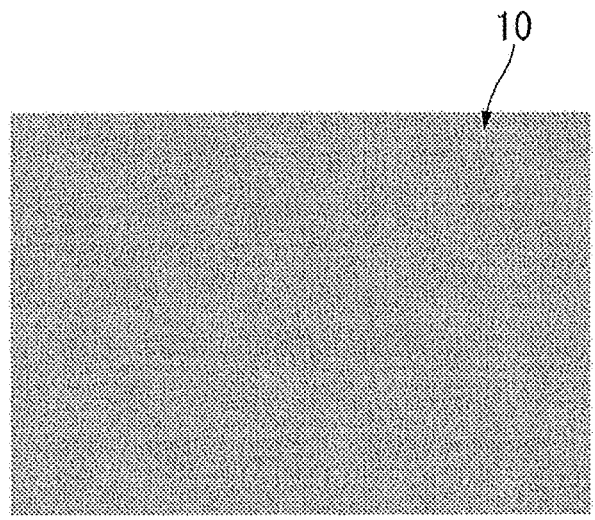
FIG. 7 is an image of an experiment example related to light transmittance of a cover member of a reaction container according to an embodiment of the present invention, and illustrates the results of bright-field observation using a reaction container having a configuration corresponding to a case where the cover member does not have light transmittance.
Figure 8:
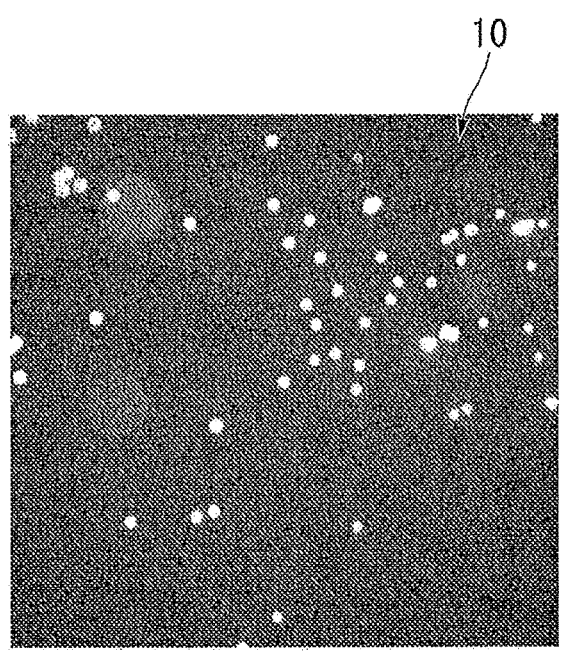
FIG. 8 is an image of an experiment example related to light transmittance of a cover member of a reaction container according to an embodiment of the present invention, and illustrates the results of fluorescence observation using a reaction container having a configuration corresponding to a case where the cover member does not have light transmittance.

FIG. 7 is an image of an experiment example related to light transmittance of the cover member of the reaction container according to an embodiment of the present invention, and illustrates the result of bright-field observation using a reaction container having a configuration corresponding to the case where the cover member is not transparent. FIG. 8 is an image of an experiment example related to light transmittance of the cover member of the reaction container according to an embodiment of the present invention, and illustrates the result of fluorescence observation using a reaction container having a configuration corresponding to the case where the cover member is not transparent.

As illustrated in FIG. 7 and FIG. 8, in the case where the non-transparent black film is also applied to the reaction container 10 for experimentation, an image could not be obtained by bright-field observation. However, in this case, an image could be obtained by fluorescence observation.

An embodiment according to the present invention was explained in detail above with reference to the drawings. However, specific configurations are not limited to this embodiment, and design changes and the like within a range not deviating from the spirit of the present invention are also included.

For example, the reaction container according to the embodiment described above may further include detection electrodes (not illustrated in the drawings) arranged inside the recessed portions so that contact is made with the liquid accommodated in the recessed portions. The detection electrodes can be connected to a measuring device by wiring (not illustrated in the drawings), and can be used for pH measurement and other electrochemical measurements.

In addition, the reaction container according to the embodiment above may have a plurality of regions that include a plurality of recessed portions on the first surface. The plurality of regions in this case becomes a plurality of reaction zones independent from each other. In other words, samples that are different from each other can be supplied to the plurality of reaction zones so that one type of sample corresponds to one region that is one reaction zone. The outer perimeters of these plural regions are surrounded by spacer portions, and by welding the spacer portions to the cover member, regions are formed in which biochemical analysis can be performed without mixing of the samples. By setting a plurality of reaction zones on the base as described above, analysis conditions (temperature, reaction time and the like) for the plurality of samples can be set.

Moreover, the cover member may have a light transmittance in part of a range of the wavelength band of visible light that is higher than the light transmittance in other ranges of the wavelength band of visible light. For example, the cover member may have a light transmittance of 25% or more in a range of 480 nm or more and 570 nm or less in the wavelength band of visible light. When the light transmittance of the cover member is 25% or more in a range of 480 nm or more and 570 nm or less in the wavelength band of visible light, green fluorescence and the like can be easily observed.

EXAMPLES

Example 1

Example 1 will be described below.

In the laser transmission welding method, a light transmitting material that transmits laser light having a specified wavelength and a light absorbing material that absorbs this laser light are placed together and pressure is applied from both sides, then the above-mentioned laser light is irradiated from the transmitting material side onto the boundary surfaces of the transmitting material and the absorbing material by which the absorbing material is caused to melt. In doing so, the absorbing material melts, heat is also transmitted from the absorbing material to the transmitting material, and by heating the transmitting material to a temperature that exceeds the melting temperature of the transmitting material, the transmitting material also melts. As a result, in the laser transmission welding method, a transmitting material having light absorbance that is low with respect to the wavelength of the irradiated laser light can also be welded.

In this example, a specific example is given in which, together with being able to reliably weld the cover member that functions as an absorbing material when manufacturing the reaction container by using the laser transmission welding method to the base by the laser transmission welding method, fluorescence observation is possible by fluorescence that is transmitted by the cover material in a biochemical reaction using the reaction container.

The material of the base in this example is cycloolefin polymer (COP) (1 mm thickness).

A cover member was manufactured using polystyrene (black) and PMMA (YL-500P-Y1 YAG (translucent), manufactured by SIGMAKOKI Co., Ltd.) as the material of the cover member in this example.

As a Comparative Example in which the material of the cover member is indicated as not suitable for the laser transmission welding method, the material polystyrene (transparent), PMMA (YL-500P-LD (translucent)), and PMMA (YL-500P-Y2 argon (translucent)) are also indicated. These materials have low absorbance to a YAG laser.

As a laser welding machine in this Example and Comparative Example, a YAG laser welding machine ML-2030B (manufactured by AMADA MIYACHI) was used.

In this example, after bringing the base and the cover member into close contact, the ends of both materials were gripped with a turn clip and arranged so that the base side faced upward. After that, the laser welding machine was set so as to irradiate the laser perpendicularly from the base side.

Laser welding was performed for all combinations of the above-described materials selected as the base and the cover member. As the settings for performing laser welding, the irradiation voltage was 400V, the irradiation time was 1 ms, the number of irradiations was 10 times/second, and laser light was irradiated at three locations that were separated from each other.

As a result, welding was possible in the cases where polystyrene (black), and PMMA (YL-500P-Y1 YAG (translucent) were used as the material of the cover member.

Next, a green filter was placed on each material used for the cover member and white light was passed through the material, and whether or not the light could be visually recognized from the opposite side of the cover member was checked.

As a result, light could be visually recognized for all of the materials except for polystyrene (black).

From the above, it was confirmed that by using a combination of COP and PMMA (YL-500P-Y1 YAG (translucent)) as the materials of the base and the cover member, respectively, laser welding could be performed, and that a material configuration in which light can be detected from the cover member side can be achieved.

The material of the base may also be a light transmitting resin other than COP.

Example 2

Example 2 will be described below.

In this example, a specific example is given in which, together with being able to reliably weld the cover member that functions as an absorbing material when manufacturing the reaction container by using the laser transmission welding method to the base by the laser transmission welding method, fluorescence observation is possible by fluorescence that is transmitted by the cover material in a biochemical reaction using the reaction container.

The material of the base in this Example is cycloolefin polymer (COP) (0.3 mm to 1 mm thickness). A cover member was manufactured using carbon-added COP material (black: 0.01%, 0.1%, 0.8%, 6%, 24%, 47% transmittance) as the material of the cover member in this Example. Carbon-added (carbon-containing) COP material can be prepared by selecting a material from commercially available carbon material for resin (plastic) coloring, and mixing that material in at the time of making the COP material. As a Comparative Example in which the material of the cover member is indicated as not being suitable for the laser transmission welding method, a transparent COP material (91% transmittance with respect to air) to which carbon is not added for coloring was used. In addition, as a Comparative Example in which the material of the cover member is indicated as not being suitable for bright-field observation, a COP material having 0% transmittance was used.

<Measurement of Transmittance>

Measurement of the total light transmittance (optical density) was performed by using a laser light source (two wavelengths: 532 nm, 632 nm; output: approximately 2 mmW), a pinhole, a mirror, a sample holder, and a PD photodetector (OPTICAL POWER METER ML910B, manufactured by Anritsu) that were set up on an optical bench to measure the transmittance. The total light transmittance is a relative value, with the transmittance of air taken to be 100%.

As the laser welding machine used in this Example and Comparative Example, a welding machine using a semiconductor laser (LD-HEATER) manufactured by Hamamatsu Photonics having a wavelength of 940 nm was used. In this Example, the base and the cover member were placed closely together on a metal stage on which the air cylinder for welding was placed, after which the air cylinder was pressurized to press the base and the cover member closely against a transparent glass plate. After that, laser welding was performed by scanning with the laser head using a robot arm so that the laser was irradiated perpendicularly onto the glass plate.

Laser welding was performed for all combinations of the above-described materials selected as the base and the cover member. The settings for performing laser welding were, for example, the laser power, the scanning speed, the number of repetitions, and the like.

Next, a green filter was placed on each material used for the base and white light was passed through the material, and whether or not the light could be visually recognized from the opposite side of the cover member was checked. As the light source and filter, a light source and filter may be used so as to emit light having a wavelength that is similar to the wavelength of the light emitted by the target to be analyzed. White light can be appropriately selected from among LEDs, fluorescent lamps, and the like. As the light source, a light source may be used that emits light having a wavelength that is similar to the wavelength of the light emitted by the target to be analyzed. Results of laser welding and visual recognition of light are given in Table 1. In Table 1, "○" in the welding field indicates that welding could be performed well, and "X" indicates that welding could not be performed. In addition, in Table 1, "○" in the bead observation field indicates that light could be recognized, and "X" indicates that light could not be recognized.

TABLE 1

| Transmittance (%) | Welding | Bead Observation |
|---|---|---|
| 0.00% | ○ | X |
| 0.01% | ○ | ○ |
| 0.10% | ○ | ○ |
| 0.80% | ○ | ○ |
| 6% | ○ | ○ |
| 24% | ○ | ○ |
| 47% | ○ | ○ |
| 91% | X | ○ |

As shown in Table 1, as a result of laser welding, the base and the cover member could be welded without failure of the mold when a cover member material having 0% to 47% transmittance was used. On the other hand, a material having 91% transmittance could not be welded without melting. In addition, it is confirmed that the base and the cover member can be welded without failure of the mold when the transmittance is 60% or less.

Moreover, when a material having 0.01% to 47% transmittance was used, light that is irradiated from the side of the cover member opposite to the base side could be recognized from the base side. On the other hand, when a material having 0% transmittance was used, light from the opposite side of the cover member could not be recognized.

As described above, when the cover member is formed using a COP material, good laser welding can be performed when the transmittance is set to be 0.01% to 47%, and a material configuration can be achieved in which light from the cover member side can be detected. The material of the base may also be a light transmitting resin other than COP.

Figure 9:
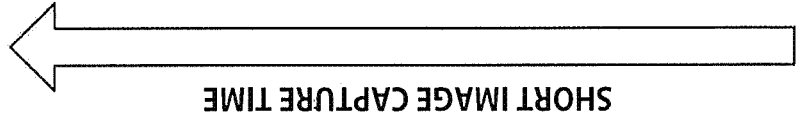
FIG. 9 illustrates images of a second example, and illustrates the results of performing bright-field observation and fluorescence observation of plural reaction containers having cover members with different light transmittances.

In addition, for each transmittance, the light exposure time was varied and images were captured in order to confirm the effect that transmittance has on the image capture time. FIG. 9 illustrates images illustrating the results of performing bright-field and fluorescence observation when varying the exposure time on a cover member having 0%, 0.1%, 24%, 47%, 91% and 100% transmittance. As a result, when the transmittance is 0.1% or more, a clear bright-field image was obtained with an exposure time of no longer than 1 second. On the other hand, when the transmittance is lower than 0.1%, an exposure time of longer than 1 second is necessary, and a longer image capture time is required in order to obtain a bright-field image.

The present application addresses the following; a microarray reaction container having a flow path can be manufactured by welding together a plurality of resin members. In digital analysis such as digital PCR or the like, a reaction state inside a reaction container is sometimes observed by using visible light or fluorescence, and light transmittance in the reaction container is sometimes required. As a technique for welding together resin members with high accuracy, a laser transmission welding method of laser welding a resin member having light transmittance and a resin member having light absorbance is known. However, among plural resin members welded by a laser transmission welding method there is a resin member having light absorbance, so the overall light transmittance is low, and there is a problem that in the case of performing bright-field observation using visible light, the field of view becomes dark.

An aspect of the present invention is to provide a reaction container that, together with being composed of resins having light transmittance that are welded together with high accuracy, is capable of obtaining sufficient brightness in bright-field observation, and to provide a biochemical analysis method that uses the reaction container.

A reaction container according to a first aspect of the present invention includes a transparent base having a plurality of recessed portions open on a first surface, and a cover member having infrared absorbance that is welded to the base outside a region of the first surface that includes the plurality of recessed portions so that inside the region a gap is formed between the first surface and the cover member, wherein the cover member transmits light in at least part of the visible light wavelength range.

In the above-described first aspect, the cover member may have light transmittance of 25% or more in a range of 480 nm or more and 570 nm or less in the wavelength band of visible light.

In the above-described first aspect, infrared absorbance on the first surface side of the cover member may be highest in a direction perpendicular to the first surface.

In the above-described first aspect, there may further be detection electrodes arranged inside the recessed portions so as to be capable of contact with liquid accommodated inside the recessed portions.

In the reaction container according the above-described first aspect, a plurality of the regions may be provided on the first surface, and the perimeter of each of the plurality of the regions may be welded to the cover member so that the plurality of regions becomes a plurality of reaction zones independent of each other.

In the first aspect, the cover member may have a total light transmittance of 0.01% to 60%.

The biochemical analysis method according to a second aspect of the present invention is a biochemical analysis method that uses a reaction container according to the above-described first aspect, and includes: a liquid feeding step of feeding a diluted liquid sample into the gap between the base and the cover member so that one target substance to be detected enters into the recessed portions; a sealing step of feeding an oil-based sealant liquid into the gap to individually seal the recessed portions; a first observation step of performing bright-field observation after the sealing step on the sample inside the recessed portions using light in the part of the range; and a second observation step of irradiating an excitation light after the sealing step through the base onto the sample inside the recessed portions, and observing fluorescence emitted by the sample corresponding to the excitation light.

The biochemical analysis method according to the above-described second aspect may further include a reaction step of performing a signal amplification reaction inside the recessed portions after the sealing step and before the second observation step.

In the above-described second aspect, the signal amplification reaction may be an enzymatic reaction.

In the above-described second aspect, the enzymatic reaction may be an isothermal reaction.

In the above-described second aspect, the enzymatic reaction may be an Invader reaction.

In the above-described second aspect, the sample may include DNA, RNA, miRNA, mRNA, or protein as a target object to be analyzed, and a specific labeling substance for the target object to be analyzed.

In the above-described second aspect, the target object to be analyzed may be a nucleic acid, and the specific labeling substance may be any one of a nucleic acid different from that of the target object to be analyzed, an enzyme, a particle, an antibody, and a liposome.

Examples of the particle include a polymer bead, a magnetic bead, a fluorescent bead, a fluorescently labeled magnetic bead, a silica bead, and a metal colloid.

In the above-described second aspect, the sealant liquid may include at least one of a fluorine-based oil and a silicone-based oil.

With the reaction container according to the above-described aspects of the present invention, resin having light transmittance can be welded with high accuracy, and sufficient brightness can be obtained in bright-field observation.

With the biochemical analysis method according to the above-described aspects of the present invention, bright-field observation and fluorescence observation can be performed using the above-described reaction container.

REFERENCE SIGNS LIST

1 . . . Reaction container
2 . . . Base
2A . . . First plate-shaped member
3 . . . Recessed portion
4 . . . Cover member
4A . . . Second plate-shaped member
5 . . . Spacer portion
10 . . . Reaction container for experimentation Obviously, numerous modifications and variations of the present invention are possible in light of the above teachings. It is therefore to be understood that within the scope of the appended claims, the invention may be practiced otherwise than as specifically described herein.

What is claimed is:

1. A reaction container, comprising:
a transparent base comprising a resin material and having a first surface and a plurality of recessed portions formed in at least one region of the first surface and recessed from the first surface; and
a cover member comprising a thermoplastic resin material and positioned on the transparent base such that the cover member is configured to form a flow path comprising a gap extending over the plurality of recessed portions between the cover member and the first surface of the transparent base and has a spacer portion welded by laser irradiation to the transparent base outside the at least one region in which the plurality of recessed portion is formed,
wherein the thermoplastic resin material of the cover member includes an additive that increases absorption of infrared light such that the thermoplastic resin material absorbs infrared light and transmits light having a wavelength within a range of visible light and that the cover member has a total light transmittance of 0.01 to 47%.

2. The reaction container of claim 1, wherein the cover member has light transmittance of 25% or more in a range of from 480 nm to 570 nm.

3. The reaction container of claim 1, wherein the cover member has a light transmittance gradient in a thickness direction of the cover member and is configured to absorb the infrared light such that a highest infrared absorbance is on an inner side of the cover member facing the transparent base in a direction perpendicular to the first surface of the transparent base.

4. The reaction container of claim 1, further comprising:
a plurality of detection electrodes positioned inside the recessed portions where a liquid sample is to be accommodated.

5. The reaction container of claim 1, wherein the transparent base is formed such that the at least one region is a plurality of regions such that each of the regions has a perimeter welded to the cover member and that the regions form a plurality of reaction zones independent of each other.

6. The reaction container of claim 1, wherein the cover member has a total light transmittance of 0.1 to 47%.

7. A method of conducting biochemical analysis, comprising:
feeding, into the flow path between the transparent base and the cover member of the reaction container of claim 1, a liquid sample such that one detection target substance included in the liquid sample enters into one of the recessed portions;
feeding an oil-based sealant liquid into the gap such that the recessed portions are independently sealed by the oil-based sealant liquid;
performing bright-field observation on the liquid sample inside the recessed portions sealed with the oil-based sealant liquid by the light having the wavelength within the range of visible light;
applying an excitation light to the liquid sample inside the recessed portions through the transparent base; and
observing fluorescence emitted by the liquid sample in response to the excitation light.

8. The method of claim 7, further comprising:
performing a signal amplification reaction inside the sealed recessed portions before the observing of the fluorescence.

9. The method of claim 8, wherein the signal amplification reaction is an enzymatic reaction.

10. The method of claim 9, wherein the enzymatic reaction is an isothermal reaction.

11. The method of claim 9, wherein the enzymatic reaction is an Invader reaction.

12. The method of claim 7, wherein the liquid sample includes, as the detection target substance, DNA, RNA, miRNA, mRNA, or protein, and further includes a labeling substance specific to the detection target substance.

13. The method of claim 12, wherein the detection target substance is a nucleic acid, and the labeling substance is one of an enzyme, a particle, an antibody, a liposome, and a nucleic acid different from a nucleic acid of the detection target substance.

14. The method of claim 7, wherein the oil-based sealant liquid includes at least one of a fluorine-based oil and a silicone-based oil.

15. The reaction container of claim 1, wherein the thermoplastic resin material of the cover member includes at least one of a cycloolefin polymer and an acrylic resin.

16. The reaction container of claim 3, wherein the cover member has a total light transmittance of 0.1 to 47%.

17. The reaction container of claim 3, wherein the cover member has a total light transmittance of 25 to 47%.

18. The reaction container of claim 4, wherein the cover member has a total light transmittance of 0.1 to 47%.

19. The reaction container of claim 1, wherein the cover member has an opening connected to the flow path.

20. The reaction container of claim 1, wherein the cover member has a light transmittance gradient in a thickness direction of the cover member such that the cover member has a lower light transmittance on an inner side facing the transparent base than an outer side on an opposite side with respect to the inner side.

* * * * *